US00PP31574P2

(12) United States Plant Patent
Hansen

(10) Patent No.: US PP31,574 P2
(45) Date of Patent: Mar. 17, 2020

(54) ***CAMPANULA* PLANT NAMED 'DELFT TEACUPS'**

(50) Latin Name: *Campanula carpatica*
Varietal Denomination: Delft Teacups

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/350,794

(22) Filed: Jan. 14, 2019

(51) Int. Cl.
*A01H 5/02* (2018.01)
*A01H 6/26* (2018.01)

(52) U.S. Cl.
USPC ..... Plt./414
CPC ..... *A01H 6/264* (2018.05)

(58) Field of Classification Search
USPC ..... Plt./414
See application file for complete search history.

*Primary Examiner* — Anne Marie Grunberg

(57) ABSTRACT

The new and distinct bellflower plant, *Campanula* plant named 'Delft Teacups' with dense, compact, mounded habit; dark-green deltoid foliage and numerous bluish campanulate flowers with near white centers over a fourteen week period beginning in late spring. The new plant is suitable for landscaping as a specimen, en masse, or in containers.

1 Drawing Sheet

Botanical designation: *Campanula carpatica.*
Cultivar denomination: 'Delft Teacups'.

STATEMENT REGARDING PRIOR DISCLOSURES UNDER 37 CFR 1.77(B)(6)

The first public disclosure of the claimed plant was made by Walters Gardens, Inc. on Feb. 1, 2018 when the claimed plant was displayed as a photograph with short description on a website owned and operated by Walters Gardens, Inc., and the initial sales of the new plants was on Oct. 8, 2018, also by Walters Gardens, Inc. who obtained the plant and all information relating thereto, from the inventor. No plants of *Campanula* 'Delft Teacups' have been sold, in this country or anywhere in the world, nor has any disclosure of the new plant been made, more than one year prior the filing date of this application, and such disclosure within one year was either derived directly or indirectly from the inventor.

BACKGROUND OF THE PLANT

The present invention relates to the new and distinct Bellflower herein also referred to as *Campanula* 'Delft Teacups', by the cultivar name, 'Delft Teacups', or as the new plant. The new plant was crossed on May 14, 2015 from a plant in a greenhouse research facility in Zeeland, Mich., and the seed was collected in late summer of 2015. The female parent was a selected unnamed seedling from the *Campanula carptica* grex 'Rapido Blue' and the male parent was the same selected unnamed seedling from the *Campanula carptica* grex 'Rapido Blue'. The single seedling from this cross represented by 'Delft Teacups' was selected from a group of seedlings by the inventor, isolated and compared in subsequent years to other *Campanula* and subsequently found to be different from all cultivars known to the discoverer and eventually given the breeder code 15-4-1.

Asexual propagation at the same nursery in Zeeland, Mich., USA by basal cuttings has shown 'Delft Teacups' to be stable and reproduce true to type in successive generations since late June 2016.

SUMMARY OF THE PLANT

*Campanula* 'Delft Teacups' has not been observed in all possible environmental conditions. The phenotype may vary slightly with changes in environments such as light intensity, fertility, water availability, etc. without, however any variation in genotype.

*Campanula* 'Delft Teacups' is distinct from all cultivars known to the inventor in the following traits:

1. Small, cordate, serrate, medium-green foliage with compact height and dense mounded habit.
2. Heavily-branched with bluish bell-shaped flowers with near white centers clustered at the nodes and ends of stems.
3. Dark-green cordate to deltoid foliage.
4. Long flowering period beginning in late spring and continuing for about 14 weeks.

Plants of *Campanula* 'Delft Teacups' are most similar to plants of the seed variety 'Rapido Blue' (not patented). 'Rapido Blue' has a shorter flowering season, less flower coverage in peak flower and the flowers are not as white in the center. The copending 'Violet Teacups' U.S. Plant patent application Ser. No. 16/350,795 has similar flower coverage in peak season and similar flowering period, but has violet bell-shaped flowers that are violet and not as white in the center. *Campanula lactiflora* 'Delft Blue' (not patented) is nearly three times as tall and twice as wide in habit and has a much shorter flowering season.

BRIEF DESCRIPTION OF THE DRAWINGS

The color drawings illustrate the overall characteristics of *Campanula* 'Delft Teacups' as a two-year-old plant. The colors are as true as reasonably possible given the technology available. The color values may vary slightly depending on light intensity and quality.

DETAILED BOTANICAL DESCRIPTION

Figure 1:
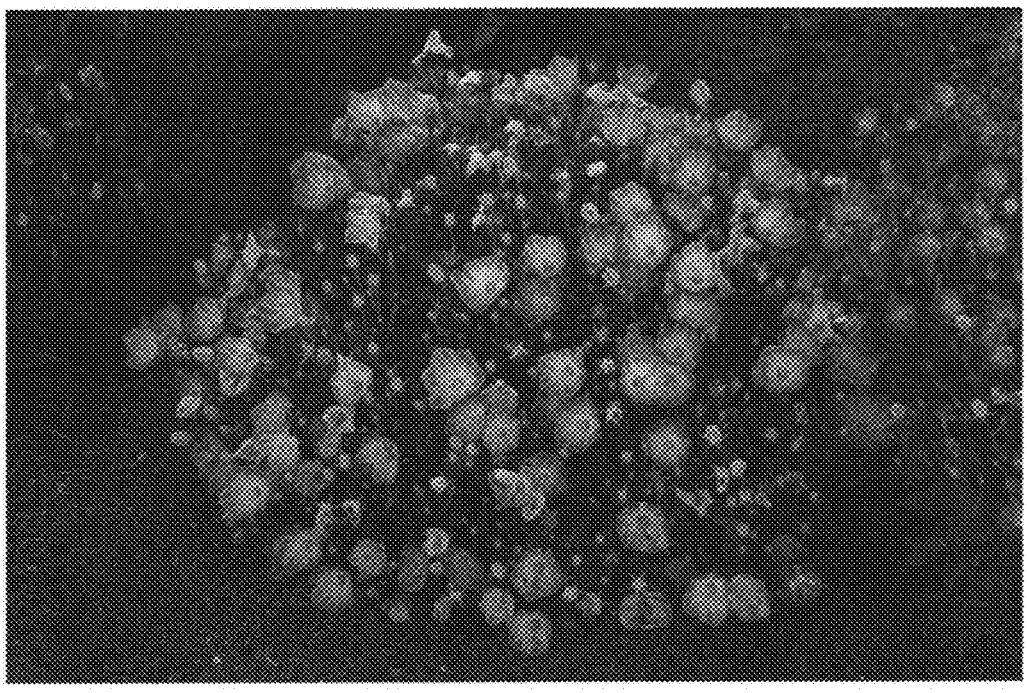
FIG. 1 shows the new plant in a landscape environment.
Figure 2:
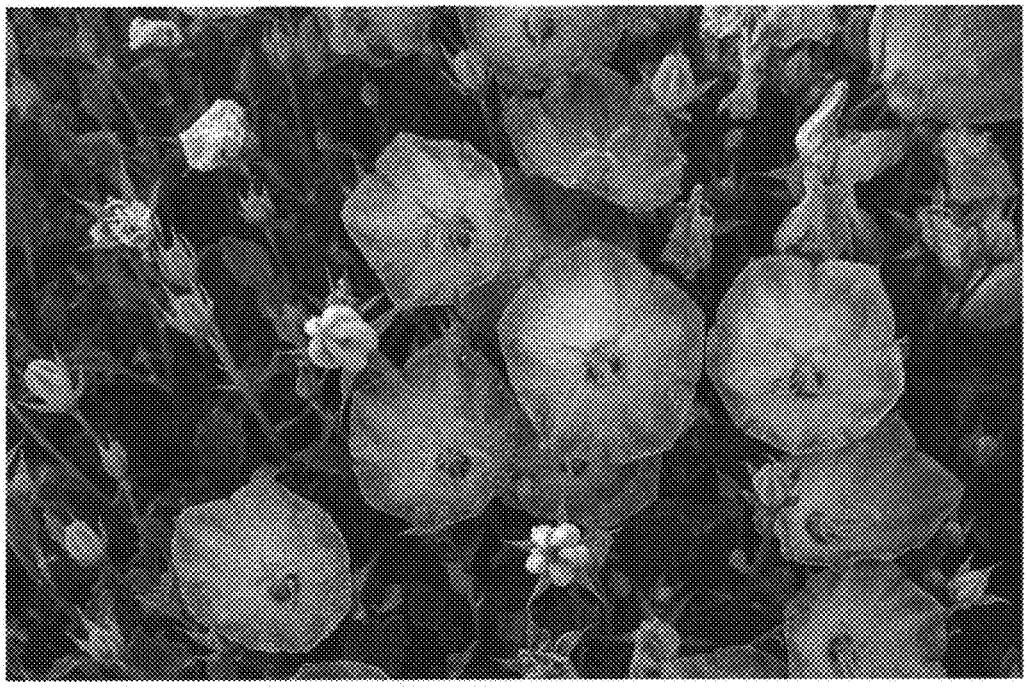
FIG. 2 shows a close-up of the flowers and buds of the new plant.

The following description is based on one and two-year-old plants growing in a full-sun trial garden and a partially shaded greenhouse in Zeeland, Mich., USA. Environmental conditions for the growing season daytime temperatures range between 12° C. to 35° C., and night temperatures range between 6° C. to 24° C. Except for ordinary dictionary color usage, color references are according to The Royal Horticultural Society Colour Chart, 2015 edition. The new plant has not been observed in all possible growing conditions and may vary in phenotypic characteristics based on water availability, light conditions, fertilizer, temperatures, etc. without varying in genotypic characteristics.

Parentage: Female or seed parent a selection of 'Rapido Blue'; male or pollen parent was the same select seedling of 'Rapido Blue';

Asexual propagation: Cuttings, about 12 to 20 days to initiate roots; time to finish in a one-gallon container about 12 weeks from an established 25 mm plug;

Plant habit: Rounded mound, herbaceous, perennial, winter-hardy; with heavily-branched flower stems up to 42.0 cm wide and 20.0 cm tall; average about 40.0 cm across and about 18.0 cm tall; with about 6 well-branched stems per plant;

Roots: Finely branched; color nearest RHS NN155B;

Stems: Flexible; glabrous; thin; cylindrical with slight longitudinal ridges; to about 18.0 cm long and 3.0 mm diameter at base;

Stem color: Young stems blend of nearest RHS 183B and RHS 146D, mature stems nearest RHS 146D toward base and nearest RHS 146B distally;

Leaves: Cauline alternate; simple; cordate to deltoid; acute apex; truncate to cordate base; margin serrate teeth curved toward apex; adaxial and abaxial surfaces glabrous, matte; up to 28.0 mm long and 26.0 mm wide, average about 20.0 mm long and 22.0 mm wide;

Leaf color: Young expanding leaves adaxial nearest RHS 146C with slight bronze blush of nearest RHS 175D and abaxial nearest RHS 146D with slight bronze blush of nearest RHS 175D; mature leaves adaxial between RHS 137A and RHS 137B, abaxial nearest RHS 137B;

Petiole: Thin; concavo-convex; glabrous both adaxial and abaxial; margin entire; to about 52.0 mm long and 2.5 mm wide at base;

Petiole color: Emerging leaves nearest blend of RHS 176C and RHS 146C adaxial and abaxial, mature leaves adaxial and abaxial nearest RHS 137B along margins and nearest RHS 138B in center;

Veins: Palmate;

Vein color: Adaxial midrib nearest RHS 193A, main and secondary veins nearest RHS 137A, abaxial midrib nearest RHS 145B and main and secondary veins nearest RHS 138A;

Flower: Single; perfect; shallowly campanulate; on terminal branches; to about 48.0 mm across, about 18.0 mm tall; attitude outright to upright;

Inflorescence fragrance: Not detected;

Calyx: Reflexed; to about 14.0 mm wide and extending about 8.0 mm below corolla base;

Sepals: Typically six; lanceolate; narrowly acute apex to apiculate; truncate base; margin micro-serrulate; glabrous adaxial and abaxial; about 7.5 mm long and about 1.5 mm wide at base;

Sepal color: Abaxial and adaxial nearest RHS 137B;

Flowering period: Beginning late spring, for about 14 weeks; producing about 100 flowers and 140 buds per plant at one time during peak flowering;

Flower longevity: About 5 days;

Flower buds: One day prior to opening — oblong; longitudinally channeled; rounded apex; about 14.0 mm long and 6.0 mm diameter; four days prior to opening — about 7.0 mm long and 3.5 mm diameter near apex;

Flower bud color: One day prior to opening — nearest RHS 145A; four days prior to opening — between RHS 145B and RHS 145C;

Peduncle: About 6 per plant; highly branched; cylindrical; glabrous; upright to outright attitude; flexible; about 3.0 mm diameter at base and 22.0 cm long; about 14 nodes, average internode spacing about 1.6 cm; branches to about 15.0 cm long and 2.0 mm diameter at base;

Peduncle color: Nearest 146C;

Pedicel: Cylindrical; glaucous; thin, flexible; average about 4.0 cm long and 0.5 mm diameter;

Pedicel color: Nearest RHS 144A;

Petals: Typically six, or five, rarely seven; acute apex; basal 14.0 mm fused; glabrous adaxial and abaxial; about 23.0 mm long and 16.0 mm wide above fusion;

Petal color: Adaxial nearest RHS N88D with center eye developing to lighter than RHS 85D; abaxial nearest RHS N88D with three midrib nearest RHS 85D;

Androecium: Typically five;

*Filament*.—About 5.0 mm long and 1.0 mm wide at base, puberulent, flattened and adpressed along ovary in distal one-half; glabrous distally; color nearest RHS 157C.

*Anther*.—Lanceolate; about 4.0 mm long and 1.5 mm across; color nearest RHS 61D.

*Pollen*.—Not abundant; color between RHS 163C and RHS 163D.

Gynoecium: Syncarpous; half-inferior; about 18.0 mm long;

*Style*.—Cylindrical; about 14.0 mm long and 0.5 mm diameter; color nearest RHS 145C.

*Stigma*.—Typically trifid; cochleate distally with maturity; about 4.0 mm long straightened, 2.0 mm long naturally and 0.5 mm diameter; color nearest RHS 145C.

Fruit: Oblong poricidal capsule; longitudinally carinate; 8.0 mm tall and 5.0 mm wide;

Fruit color: Nearest RHS 199C with carinate nearest RHS 161D;

Seed: Flattened ellipsoidal; rounded apex and base; about 1.0 mm long and 0.5 mm across center;

Seed color: Variable, some seeds nearest RHS 199A and others nearest RHS 199B; *Campanula* 'Delft Teacups' is tolerant of winter temperatures from USDA hardiness at least to zones 4 to 8. The new plant grows best in full sun with good drainage and adequate moisture. It is not known to be tolerant of diseases and pest that are common to other *Campanula* cultivars.

I claim:

1. The new and distinct cultivar of *Campanula* plant named 'Delft Teacups' as described and illustrated.

* * * * *